US012736510B2

(12) United States Patent
Kang et al.

(10) Patent No.: US 12,736,510 B2
(45) Date of Patent: Sep. 15, 2026

(54) ENVIRONMENTAL MONITORING DEVICE USING SMART PHONE

(71) Applicant: DEEPVISIONS CO., LTD., Seoul (KR)

(72) Inventors: Bong Su Kang, Seoul (KR); Jun Sang Cho, Seoul (KR); Min Ho Kang, Seoul (KR); Jung Woo Yoo, Seoul (KR)

(73) Assignee: DEEPVISIONS CO., LTD., Seoul (KR)

(*) Notice: Subject to any disclaimer, the term of this patent is extended or adjusted under 35 U.S.C. 154(b) by 341 days.

(21) Appl. No.: 18/396,862

(22) Filed: Dec. 27, 2023

(65) Prior Publication Data

US 2025/0208106 A1 Jun. 26, 2025

(30) Foreign Application Priority Data

Dec. 22, 2023 (KR) ........................ 10-2023-0190149

(51) Int. Cl.
*G01N 33/00* (2006.01)
*G01N 15/075* (2024.01)
(Continued)

(52) U.S. Cl.
CPC ....... *G01N 33/0075* (2013.01); *G01N 15/075* (2024.01); *G01N 21/94* (2013.01);
(Continued)

(58) Field of Classification Search
CPC .. G01N 15/0227; G01N 15/06; G01N 15/075; G01N 2015/0096; G01N 21/94; G01N 2201/0221; G01N 2201/0231; G01N 2201/0245; G01N 33/0034; G01N 33/0063; G01N 33/0067; G01N 33/0068;
(Continued)

(56) References Cited

U.S. PATENT DOCUMENTS 9,325,366 B1 * 4/2016 Zhou .................... H04B 1/3888
2014/0274232 A1 * 9/2014 Tages .................. H04B 1/3888 455/575.8

(Continued)

FOREIGN PATENT DOCUMENTS

CN 206074839 U * 4/2017 ............... G01N 1/04
KR 10-2013-0047397 A 5/2013

(Continued)

OTHER PUBLICATIONS

Lee et al, Assessment of Smartphone-Based Technology for Remote Environmental Monitoring and its Development, Instrumentation Science and Technology, 40:504-529, 2012 (Year: 2012).*

(Continued)

*Primary Examiner* — David L Singer
(74) *Attorney, Agent, or Firm* — The PL Law Group, PLLC

(57) ABSTRACT

An environment monitoring device includes a first case, a second case coupled to the first case, and a smart phone provided fixed in an inner space between the first case and the second case, wherein the smart phone is configured to measure a fine dust concentration around the environment monitoring device based on an image photographed with a camera, and display information on the measured fine dust concentration via a screen of the smart phone.

13 Claims, 9 Drawing Sheets

(51) Int. Cl.

| | |
|---|---|
| ***G01N 21/94*** | (2006.01) |
| ***G08B 17/10*** | (2006.01) |
| ***G08B 21/14*** | (2006.01) |

(52) U.S. Cl.

CPC ..... *G01N 33/0034* (2013.01); *G01N 33/0063* (2013.01); *G01N 33/0067* (2013.01); *G08B 17/10* (2013.01); *G08B 21/14* (2013.01); *G01N 33/0068* (2024.05); *G01N 2201/0221* (2013.01); *G01N 2201/0231* (2013.01); *G01N 2201/0245* (2013.01)

(58) Field of Classification Search

CPC ...... G01N 33/0075; G06N 3/08; G06Q 50/10; G08B 17/10; G08B 21/12; G08B 21/14; G08C 17/02; H04N 23/57

See application file for complete search history.

(56) References Cited

U.S. PATENT DOCUMENTS

| | | | | |
|---|---|---|---|---|
| 2016/0248965 | A1* | 8/2016 | Fukuya | H04N 21/43637 |
| 2020/0412857 | A1* | 12/2020 | Shin | H04M 1/0277 |
| 2023/0156316 | A1* | 5/2023 | Kang | H04M 1/72439<br>348/333.02 |
| 2024/0029457 | A1* | 1/2024 | Kim | G06N 3/0464 |

FOREIGN PATENT DOCUMENTS

| | | | | | |
|---|---|---|---|---|---|
| KR | 20130047397 | A | * | 5/2013 | H04N 23/51 |
| KR | 101707230 | B1 | * | 2/2017 | G08B 21/18 |
| KR | 101952122 | B1 | * | 2/2019 | G06T 7/001 |
| KR | 102233402 | B1 | * | 3/2021 | G06T 7/90 |
| KR | 10-2021-0120235 | A | | 10/2021 | |
| KR | 20210120235 | A | * | 10/2021 | G06N 3/08 |
| KR | 102326208 | B1 | * | 11/2021 | G06T 17/05 |
| KR | 20220057025 | A | * | 5/2022 | G01N 15/0227 |
| KR | 20220057026 | A | * | 5/2022 | G01N 15/0227 |
| KR | 102427039 | B1 | * | 7/2022 | G01N 15/0227 |
| KR | 20-2022-0002360 | U | | 10/2022 | |
| KR | 20220002360 | U | * | 10/2022 | G01N 33/0063 |

OTHER PUBLICATIONS

Liu et al, PM2:5 Monitoring using Images from Smartphones in Participatory Sensing, The First International Workshop on Smart Cities and Urban Informatics, IEEE 2015 (Year: 2015).*

Sung et al, Development of Local Air Pollution Observation Technology Based on Artificial Intelligent Image Analysis, 2020 IEEE (Year: 2020).*

Nemati et al, Opportunistic Environmental Sensing with Smartphones: a Critical Review of Current Literature and Applications, Current Environmental Health Report (2017) 4:306-318, Springer (Year: 2017).*

Yue et al, Effective and Efficient Photo-Based PM2.5 Concentration Estimation, IEEE Transactions on Instrumentation and Measurement, vol. 68, No. 10, Oct. 2019 (Year: 2019).*

* cited by examiner

FIRST CONVERTED IMAGE (HS CHANNEL)

FIRST CONVERTED IMAGE (S CHANNEL)

SECOND CONVERTED IMAGE

SECOND CONVERTED IMAGE(TRANSMITTANCE)

REGION OF INTEREST IMAGE

THIRD CONVERTED IMAGE

FOURTH CONVERTED IMAGE

FIFTH CONVERTED IMAGE

SIXTH CONVERTED IMAGE

ENVIRONMENTAL MONITORING DEVICE USING SMART PHONE

CROSS-REFERENCE TO RELATED APPLICATION AND CLAIM OF PRIORITY

This application claims the benefit under 35 USC § 119 of Korean Patent Application No. 10-2023-0190149, filed on Dec. 22, 2023, in the Korean Intellectual Property Office, the entire disclosure of which is incorporated herein by reference for all purposes.

BACKGROUND

1. Field

The following description relates to an environment monitoring device using a smart phone.

2. Description of Related Art

Fine dust is dust whose particles are so small that they are invisible to the eye. There are studies showing that fine dust incapacitates a defense system of the body and has various effects on the body, such as cardiovascular, respiratory, and cerebrovascular diseases, and the International Agency for Research on Cancer (IARC) under the World Health Organization (WHO) announced that fine dust was designated as a group 1 carcinogen. Due to these risks, fine dust is being analyzed as the cause of the problem of declining economic activity among members of society.

In addition, recently, the use of smart phones is increasing around the world, and upgraded smart phone products are being released at regular intervals according to users' needs. Accordingly, a large number of smart phones are being discarded without being used around the world, which causes various environmental problems.

SUMMARY

Embodiments of the present disclosure are intended to provide an environment monitoring device using a smart phone.

According to an exemplary embodiment of the present disclosure, there is provided an environment monitoring device, which is an environment monitoring device installed indoors or outdoors, including a first case, a second case coupled to the first case, and a smart phone provided fixed in an inner space between the first case and the second case, wherein the smart phone measures a fine dust concentration around the environment monitoring device based on an image photographed with a camera, and displays information on the measured fine dust concentration via a screen of the smart phone.

The first case may include a first opening provided corresponding to the size of a screen of the smart phone to expose the screen of the smart phone to the outside, and the second case may be coupled to the first case at the rear of the first case, and include a second opening provided corresponding to the camera of the smart phone.

The environment monitoring device may include a smart phone support that fixedly supports the smart phone between the first case and the second case, wherein the smart phone support may include a first support provided with a third opening to allow the smart phone to be inserted thereinto and received therein, and a second support for supporting the smart phone in front of the first support, and provided with a fourth opening corresponding to the size of the screen of the smart phone.

The environment monitoring device may further include a heat dissipation part provided on the back surface of the second case and provided to emit heat generated from the smart phone to the outside, and a gap formed in a frame of the first support.

The smart phone may include a photographing module including the camera, and allowing the camera to photograph the front, a conversion module for converting all or a part of a photographed image of the photographing module into an image having different characteristics to generate one or more converted images, a fine dust measurement module for inputting the converted image to a pre-trained deep learning model to measure a fine dust concentration at a target point of photography, and a display module for displaying information on the measured fine dust concentration on a screen.

The display module may classify a value of the measured fine dust concentration into any one level among a plurality of preset levels, and display pre-stored visual representation contents on the screen according to the classified level.

The fine dust measurement module may input a plurality of converted images of different types to the deep learning model when training the deep learning model to respectively output fine dust concentration prediction values for the plurality of converted images, train the deep learning model to minimize a difference between each fine dust concentration prediction value and a correct answer value, extract a prediction value closest to the correct answer value among the fine dust concentration prediction values, and store a type of a converted image corresponding to the extracted prediction value by matching the type with one or more of environment information and climate information at the time of the photography.

The conversion module may acquire one or more of the environment information and climate information at the time of the photography, determine into which type of an image to convert all or a part of the photographed image based on one or more of the acquired environment information and climate information, and generate a converted image by converting all or a part of the photographed image into an image of the determined type.

The smart phone may include a photographing module including the camera, and allowing the camera to photograph the front, a conversion module that performs a first-type conversion for converting all or a part of a photographed image of the photographing module into an image of different characteristics to generate a converted image, or performs a second-type conversion for converting all or a part of a photographed image into data of different types to generate converted data, and a fine dust measurement module for inputting the converted image or the converted data to a pre-trained deep learning model to measure a fine dust concentration at a target point of photography.

The environment monitoring device may be provided to be able to communicate with one or more other environment monitoring devices installed in the vicinity of the environment monitoring device, and provided to receive a fine dust information request from other environment monitoring devices.

The environment monitoring device may transmit one or more of a photographed image, a converted image, converted data, and a fine dust concentration measurement value to other environment monitoring devices in response to the fine dust information request from other environmental monitoring devices.

The environment monitoring device may transmit one or more of the photographed image, the converted image, the converted data, and the fine dust concentration measurement value to other environment monitoring devices based on a degree of network communication between the environment monitoring device and other environment monitoring devices and hardware specification information of other environment monitoring devices.

The environment monitoring device may assign a transmission score based on the degree of network communication and the hardware specification information of other environment monitoring devices, and transmit the photographed image when the transmission score falls within a preset first range, transmit the converted image when the transmission score falls within a second range lower than the first range, transmit the converted data when the transmission score falls within a third range lower than the second range, and transmit the fine dust concentration measurement value when the transmission score falls within a fourth range lower than the third range.

The environment monitoring device may be provided to perform data communication with the smart phone, and provided to monitor other environment-related information other than the fine dust concentration, and may further include a main board for displaying other environment-related information using the smart phone.

The main board may include a harmful gas measurement module for measuring a preset harmful gas concentration around the environment monitoring device, an air quality measurement module for measuring air quality around the environment monitoring device, a fire detection module for detecting a fire around the environment monitoring device, a weather measurement module for measuring a preset weather factor around the environment monitoring device, and a power supply module for supplying power to the environment monitoring device.

DETAILED DESCRIPTION

Hereinafter, specific embodiments of the present invention will be described with reference to the accompanying drawings. The following detailed description is provided to assist in a comprehensive understanding of the methods, devices and/or systems described herein. However, the detailed description is only illustrative, and the present invention is not limited thereto.

In describing embodiments of the present invention, when a specific description of known technology associated with the present invention is deemed to make the gist of the present invention unnecessarily vague, the detailed description thereof will be omitted. The terms used below are defined in consideration of functions in the present invention, but may vary in accordance with the customary practice or the intention of a user or an operator. Therefore, the terms should be defined based on whole content throughout the present specification. The terms used herein are only for describing the embodiments of the present invention, and should not be construed as limited. A singular expression includes a plural meaning unless clearly used otherwise. In the present description, expressions such as "include" or "have" are for referring to certain characteristics, numbers, steps, operations, components, and some or combinations thereof, and should not be construed as excluding the presence or possibility of one or more other characteristics, numbers, steps, operations, components, and some or combinations thereof besides those described.

Meanwhile, directional terms such as "upper side", "lower side", "one side", and "other side" are used in relation to the orientations in the disclosed drawings. Since components of the embodiments of the present invention may be positioned in various orientations, the directional terms are merely illustrative and do not limit the components.

In addition, the terms "first," "second," and the like may be used for describing various elements, but the elements should not be construed as being limited by the terms. These terms may be used for distinguishing one element from another element. For example, a first element could be termed a second element and vice versa without departing from the scope of the present invention.

Figure 1:
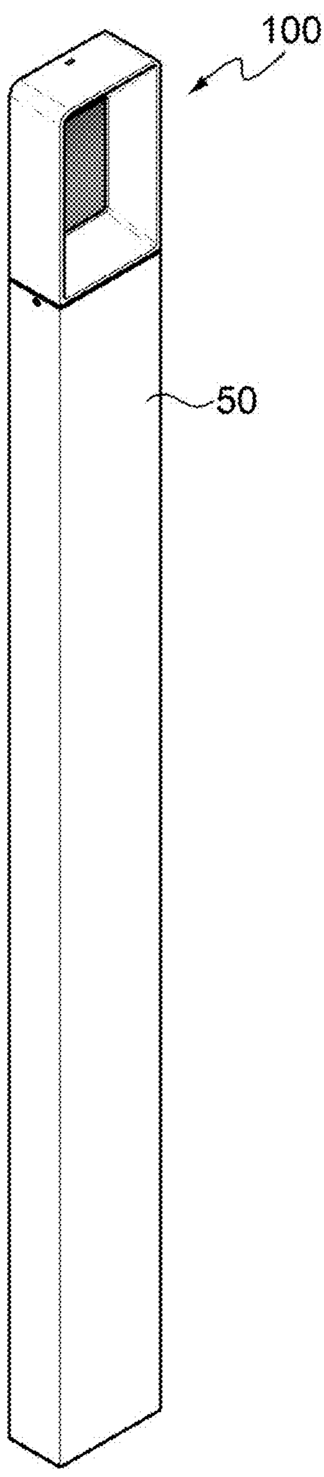
FIG. 1 is a diagram showing an appearance of an environmental monitoring device according to one embodiment of the present disclosure.
Figure 2:
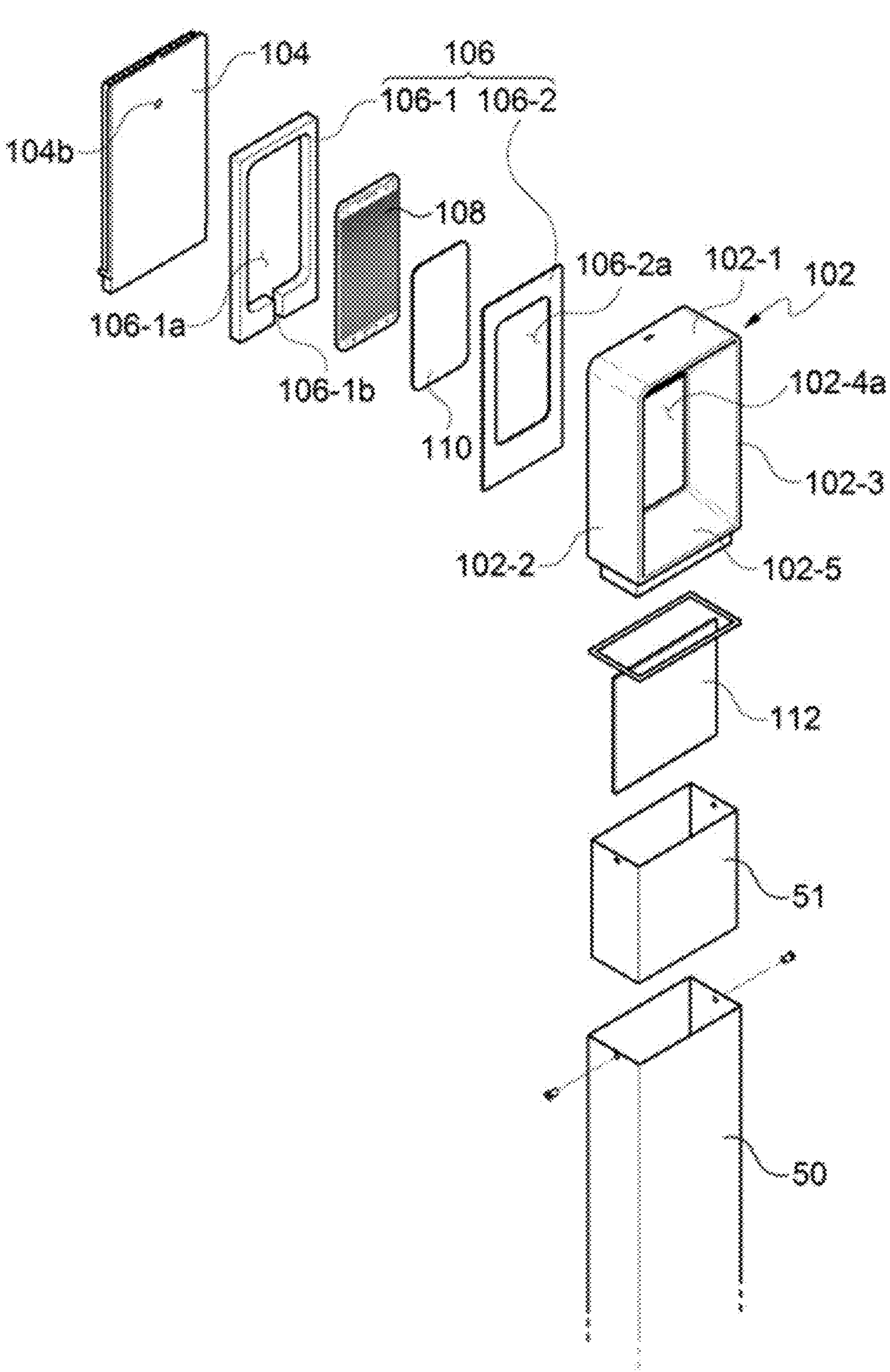
FIG. 2 is a front exploded perspective view of an environmental monitoring device according to one embodiment of the present disclosure.
Figure 3:
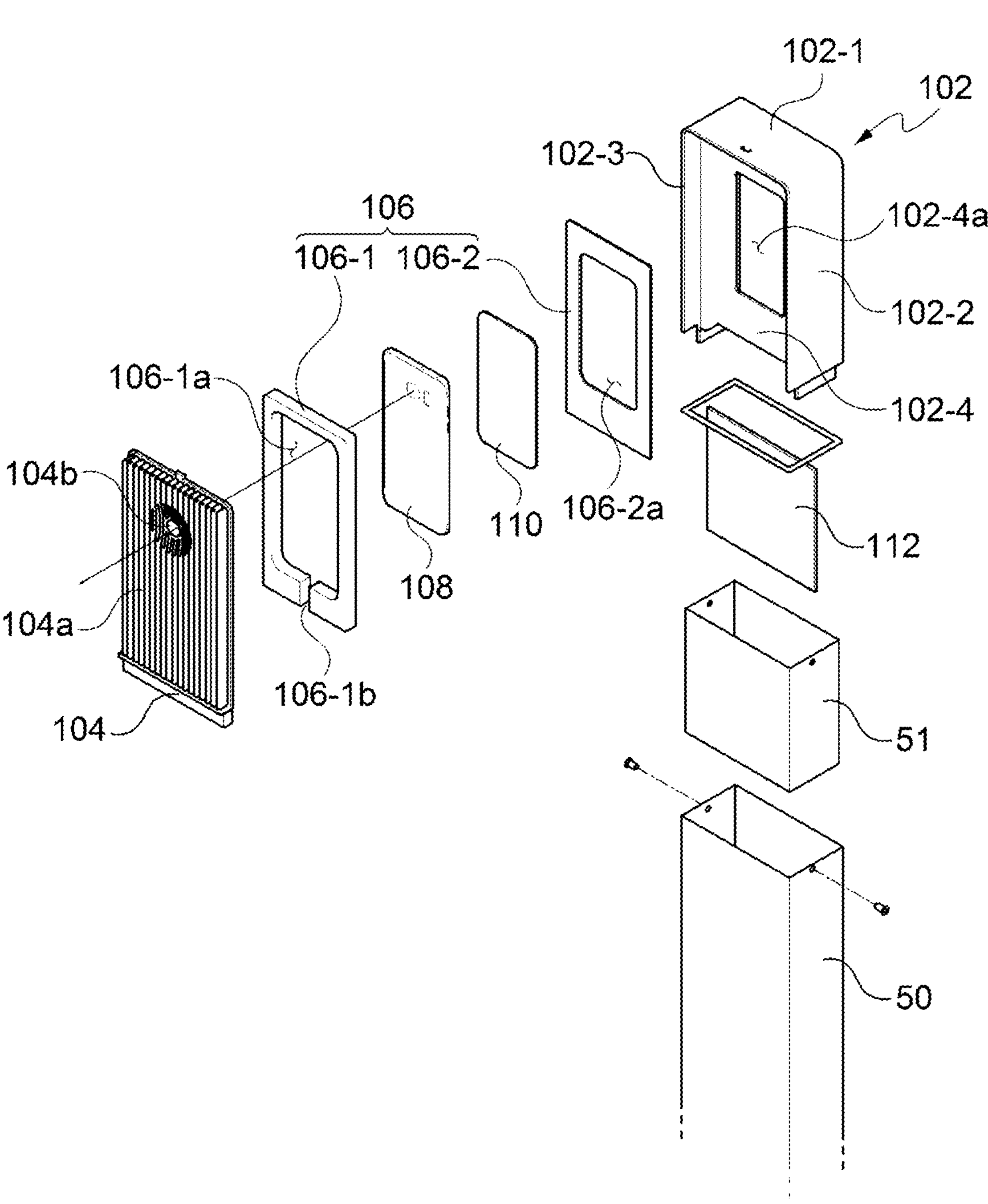
FIG. 3 is a back exploded perspective view of an environmental monitoring device according to one embodiment of the present disclosure.

FIG. 1 is a diagram showing an appearance of an environmental monitoring device according to one embodiment of the present disclosure, FIG. 2 is a front exploded perspective view of an environmental monitoring device according to one embodiment of the present disclosure, and FIG. 3 is a back exploded perspective view of an environmental monitoring device according to one embodiment of the present disclosure.

Referring to FIG. 1 to FIG. 3, an environmental monitoring device 100 may include a first case 102, a second case 104, a smart phone support 106, and a smart phone 108.

The environmental monitoring device 100 may be installed in an office, a conference room, or the like, or in a space inside a building. In addition, the environmental monitoring device 100 may be installed outdoors, such as in a park or on a road. The environmental monitoring device 100 may measure fine dust in a place in which the environmental monitoring device 100 is installed and display or notify the concentration of the fine dust. In addition, the environmental monitoring device 100 may monitor environmental information (e.g., temperature, humidity, illumination, harmful gases, air quality, etc.) of a surrounding place, and may display or notify the monitored information.

In one embodiment, the environmental monitoring device 100 may be provided coupled to an upper end of a support member 50 which is provided perpendicular to the ground. For example, the environmental monitoring device 100 may be coupled to the upper end of the support member 50 via a coupling plate 51. In this case, the environmental monitoring device 100 may be provided at a height equal to or similar to the height of people's gaze. However, the embodiment is not limited thereto, and the environmental monitoring device 100 that may be mounted on a wall or ceiling inside a building. The environmental monitoring device 100 may be installed in plurality spaced apart from each other in a predetermined area or place.

The first case 102 may constitute the exterior of a front portion and a side portion of the environmental monitoring device 100. In one embodiment, the first case 102 may include an upper plate 102-1, a first side plate 102-2, a second side plate 102-3, and an inner connection plate 102-4.

The upper plate 102-1 may be provided parallel to the ground. The upper plate 102-1 may be provided having a predetermined width. The first side plate 102-2 may be provided perpendicularly downward from one side of the upper plate 102-1. The second side plate 102-3 may be provided perpendicularly downward from the other side of the upper plate 102-1.

The inner connection plate 102-4 may be provided connecting the upper plate 102-1, the first side plate 102-2, and the second side plate 102-3 inside the first case 102. The inner connection plate 102-4 may be provided perpendicular to each of the upper plate 102-1, the first side plate 102-2, and the second side plate 102-3. A first opening **102-4*a* may be provided in a central portion of the inner connection plate 102-4. The first opening 102-4*a* may be provided corresponding to the size of a screen of the smart phone 108**.

Inclined plates 102-5 provided inclined toward the inner connection plate 102-4 may be formed in a front portion of the first case 102. The inclined plate 102-5 may be provided to have an inclination by being connected to the first opening **102-4*a* of the inner connection plate 102-4 at the front edge of the upper plate 102-1, the first side plate 102-2, and the second side plate 102-3**.

The second case 104 may be coupled to the first case 102 at the rear of the first case 102. The second case 104 may constitute the exterior of a back portion of the environment monitoring device 100. A heat dissipation part **104*a* for discharging heat generated from the smart phone 108 to the outside may be provided on a back surface of the second case 104. The second case 104 may be formed of a metal material. In one embodiment, the heat dissipation part 104*a* may have a concave-convex pattern. The concave-convex pattern may be periodically provided along a width direction of the second case 104**, but is not limited thereto.

A second opening **104*b* may be provided in the second case 104. The second opening 104*b* may be provided corresponding to a camera part of the smart phone 108. The second opening 104*b* may be provided in a diameter that allows a camera of the smart phone 108** to secure a forward view.

The smart phone support 106 may be provided between the first case 102 and the second case 104. The smart phone support 106 may be provided to be fixed in an inner space between the first case 102 and the second case 104. The smart phone support 106 may serve to support the smart phone 108.

The smart phone support 106 may include a first support 106-1 and a second support 106-2. The first support 106-1 may be provided to allow the smart phone 108 to be received therein. The first support 106-1 may be provided in the form of a rectangular frame in which a third opening **106-1*a* is provided. The third opening 106-1*a* may be provided corresponding to the size of the smart phone 108**.

The smart phone 108 may be inserted into and fixed to the third opening **106-1*a*. A gap 106-1*b* having a predetermined width may be provided in the rectangular frame of the first support 106-1. Accordingly, the smart phone 108 may be easily inserted into the third opening 106-1*a***.

The second support 106-2 may support the smart phone 108 in front of the first support 106-1. The second support 106-2 may be provided in close contact with the first support 106-1 in front of the first support 106-1. The second support 106-2 may be provided in a size corresponding to the first support 106-1.

The second support 106-2 may be provided in the form of a rectangular frame in which a fourth opening **106-2*a* is provided. The fourth opening 106-2*a* may be provided corresponding to the size of the screen of the smart phone 108. That is, the fourth opening 106-2*a* may be provided to allow the screen of the smart phone 108, which is inserted into and fixed to the third opening 106-1*a* of the first support 106-1**, to be exposed to the front.

The smart phone 108 may be provided fixed by the smart phone support 106 in the inner space between the first case 102 and the second case 104. In one embodiment, a discarded smart phone (i.e., a waste smart phone as electronic waste) may be used as the smart phone 108, but the embodiment is not limited thereto.

The smart phone 108 may include a camera on the back surface thereof. The camera may be exposed to the outside through the second opening **104*b*. A protective member 110 may be provided on the front surface of the smart phone 108. The protection member 110 may be provided to protect the screen of the smart phone 108. The protection member 110 may be provided in a size corresponding to the fourth opening 106-2*a*. The protective member 110** may be formed of a material such as a transparent film, plastic, tempered glass, or the like, but is not limited thereto.

In one embodiment, the environment monitoring device 100 may photograph the front of the camera of the smart phone 108 using the smart phone 108, measure the concentration of fine dust around the environment monitoring device 100 based on the photographed image, and display a level of the measured fine dust concentration via a screen of the smart phone 108.

Figure 4:
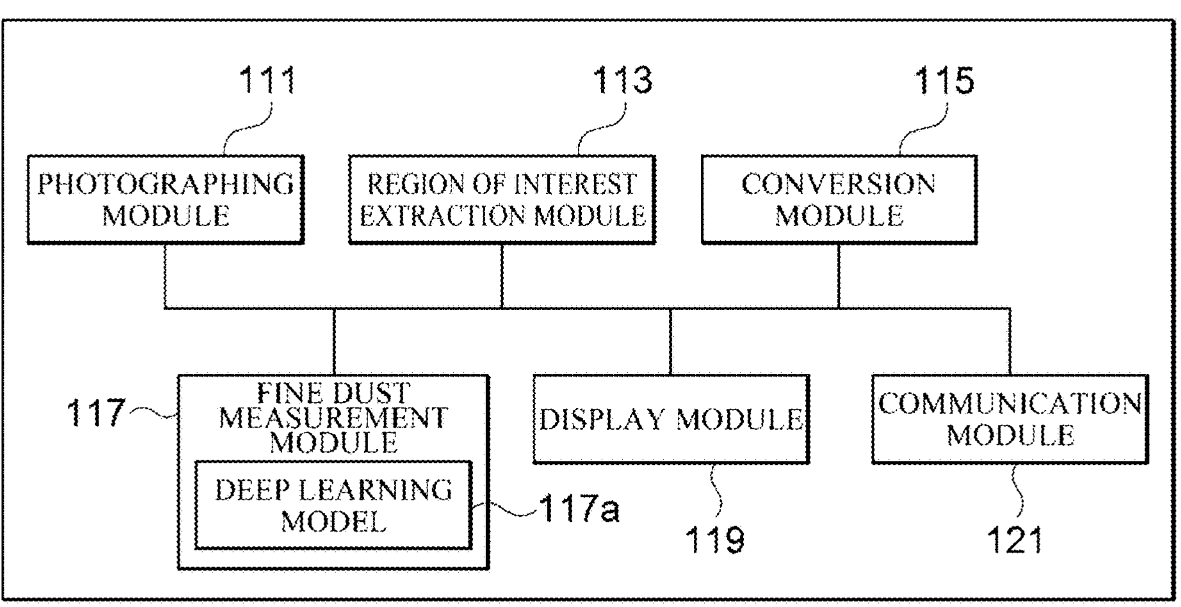
FIG. 4 is a block diagram showing a configuration of a smart phone for measuring a fine dust concentration in one embodiment of the present disclosure.

FIG. 4 is a block diagram showing a configuration of the smart phone 108 for performing the above functions. Referring to FIG. 4, the smart phone 108 may include a photographing module 111, a region-of-interest extraction module 113, a conversion module 115, a fine dust measurement module 117, a display module 119, and a communication module 121.

The photographing module 111 may include a camera. The photographing module 111 may photograph the front of the camera. For example, the photographing module 111 may photograph the front of the camera according to a preset cycle or an input command. In one embodiment, an image photographed by the photographing module 111 may be a red, green, and blue (RGB) image.

The region of interest extraction module 113 may extract a region of interest from the photographed image. The region of interest extraction module 113 may extract a boundary region of each object included in the photographed image, and if a change in pixel value within the boundary region exceeds a preset threshold value, a region including a corresponding object may be extracted as a region of interest. A technique for extracting a boundary region of an object in an image is a known technique, and thus a detailed description thereof will be omitted.

The transform module 115 may perform conversion to use an image of the region of interest as an input to the deep learning model 117*a*. The conversion module 115 may convert the image of the region of interest into one or more images having characteristics sensitive to fine dust. That is, the conversion module 115 may convert the image of the region of interest into one or more images suitable for measuring a concentration of fine dust.

In one embodiment, the conversion module 115 may convert a red, green, and blue (RGB) image of the region of interest into a hue, saturation, and value (HSV) image to generate a first converted image. Here, since the hue (H) has pure color information, the HSV image may allow a color to be classified more easily than the RGB image, and may be less affected by a change in illuminance or shade through the adjustment of a value of the value (V).

When the image of the region of interest is converted into the HSV image, the conversion module 115 may use the HSV image itself as the first converted image, may use hue (H) and saturation(S) channels from the HSV image as the first converted image, or may use only the saturation(S) channel from the HSV image as the first converted image. At this time, a value of the hue (H) or saturation(S) varies depending on the concentration of fine dust.

In addition, the conversion module 115 may apply a dark channel prior (DCP) technique to the RGB image of the region of interest, thereby performing image conversion, to generate a second converted image. When the dark channel prior (DCP) technique is applied to the RGB image of the region of interest, haze (a phenomenon in which the progression of light is interrupted by substances present between an object and a camera, causing the object to appear blurry) present in the RGB image of the region of interest may be eliminated. At this time, the image conversion module 106 may extract transmittance characteristics of the RGB image of the region of interest based on the dark channel prior (DCP) and use the same as the second converted image. The turbidity of the second converted image varies depending on the concentration of fine dust.

In addition, the conversion module 115 may apply a Garbor filter to the RGB image of the region of interest, thereby performing image conversion, to generate a third converted image. When the Gabor filter is applied to the RGB image of the region of interest, an edge may be extracted from the region of interest, and the clarity of the edge varies depending on the amount of fine dust.

In addition, the conversion module 115 may apply a Sobel filter to the RGB image of the region of interest, thereby performing image conversion, to generate a fourth converted image. The Sobel filter is a filter that performs filtering according to the directionality of a frequency in an image, and may more sensitively detect an edge in a diagonal direction rather than horizontal and vertical edges.

In addition, the conversion module 115 may apply a local binary pattern (LBP) technique to the RGB image of the region of interest, thereby performing image conversion, to generate a fifth converted image. The local binary pattern (LBP) technique converts a pixel value around each pixel of the image into a binary number (0 or 1) to extract characteristics of the image, wherein the binary number is generated according to a relative brightness difference between a center pixel and a neighboring pixel. That is, if the neighboring pixel is larger than the center pixel, the binary number is 1, and if the neighboring pixel is smaller than the center pixel, the binary number is 0.

In addition, the conversion module 115 may apply a Laplacian filter to the RGB image of the region of interest, thereby performing image conversion, to generate a sixth converted image. The Laplacian filter performs a quadratic derivative in horizontal and vertical directions of an image, through which the center of an edge (i.e., the inflection point of a change in pixel value) may be found.

Figure 5:
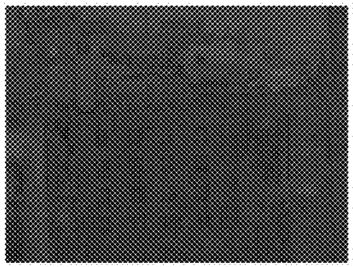
FIG. 5 is a diagram showing first to sixth converted images generated by performing first-type conversion on an image of a region of interest in one embodiment of the present disclosure.
Figure 5:
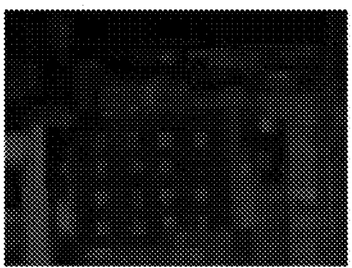
Figure 5:
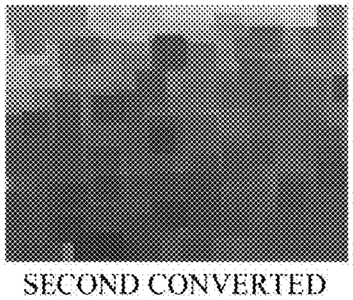
Figure 5:
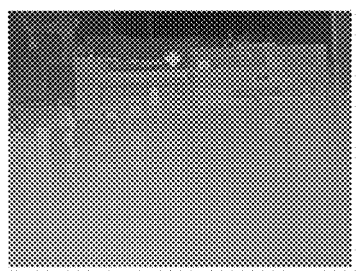
Figure 5:
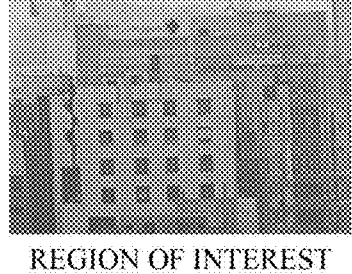
Figure 5:
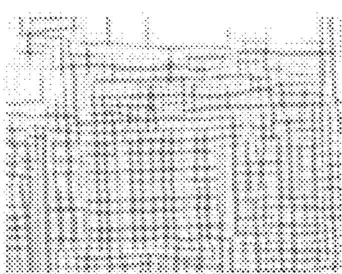
Figure 5:
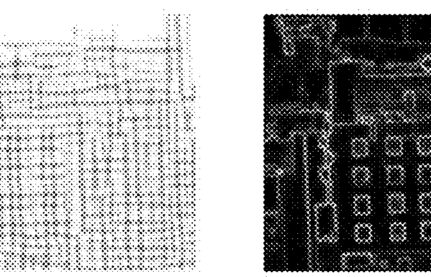
Figure 5:
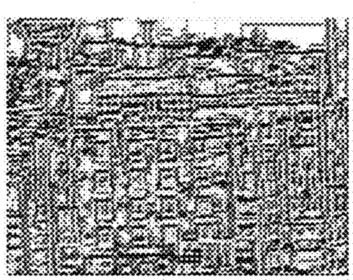
Figure 5:
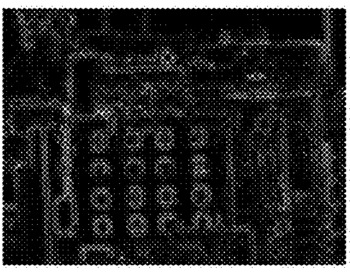

FIG. 5 is a diagram showing first to sixth converted images generated by performing a first-type conversion on an image of a region of interest in one embodiment of the present disclosure. The conversion module 115 may generate each of the first to sixth converted images based on an image of a region of interest in a training step of the deep learning model 117*a*.

Meanwhile, in an inference step for measuring the concentration of fine dust after training of the deep learning model 117*a* to be described later is completed, the conversion module 115 may determine, based on additional information that is inputted, which image conversion to perform when performing image conversion on the image of the region of interest. Here, the additional information may be environmental information or climate information of a place for measuring the concentration of fine dust. In one embodiment, the additional information may be temperature, humidity, illumination, wind speed, or the like of the place for measuring the concentration of fine dust, but is not limited thereto.

In addition, here, the conversion module 115 has been described to perform image conversion based on the image of the region of interest, but is not limited thereto, and may perform image conversion on the photographed image itself without going through the process of extracting the region of interest.

The fine dust measurement module 117 may measure a fine dust concentration at a target point of photography based on one or more converted images. At this time, the fine dust measurement module 117 may a fine dust concentration based on deep learning technology. Therefore, the fine dust measurement module 117 may include the deep learning model 117*a*.

The fine dust measurement module 117 may input one or more converted images to the deep learning model 117*a* to train the deep learning model 117*a* to predict a fine dust concentration according to a photographed image. The deep learning model 117*a* may be trained to minimize a difference between a predicted fine dust concentration and an actual measured fine dust concentration (i.e., a correct answer value).

Here, the correct answer value may be obtained from a device (e.g., a light scattering sensor, etc.) that actually measures a fine dust concentration at a target point of photography. The fine dust concentration measurement device may measure a fine dust concentration of a corresponding place according to a photographing time zone. However, the embodiment is not limited thereto, and the correct answer value may receive fine dust concentration data for a region including a site from an external agency.

In one embodiment, the fine dust measurement module 117 may be provided to measure a fine dust concentration level for each of fine dust (PM 10), ultra-fine dust (PM 2.5), and super ultra-fine dust (PM 1.0) based on a photographed image.

The fine dust measuring module 117 may input each of the first to sixth converted images to the deep learning model 117*a*. The first to sixth converted images are not simultaneously inputted, and may be sequentially inputted for each learning epoch.

The deep learning model 117*a* may receive the first converted image and output a first fine dust concentration prediction value. The deep learning model 117*a* may receive the second converted image and output a second fine dust concentration prediction value. Similarly, the deep learning model 117*a* may receive the third converted image to the sixth converted image to respectively output a third fine dust concentration prediction value to a sixth fine dust concentration prediction value. The deep learning model 117*a* may be trained to compare each of the first fine dust concentration prediction value to the sixth fine dust concentration prediction value with the correct answer value (an actual measured fine dust concentration value) to minimize a difference therebetween.

In a training process, the fine dust measurement module 117 may extract a prediction value closest to the correct answer value among the first fine dust concentration prediction value to the sixth fine dust concentration prediction value, and store a type of a converted image corresponding to the extracted prediction value by matching the type with one or more of environment information (e.g., illumination or the like of a target place) and climate information (e.g., temperature, humidity, wind speed or the like of a target place) at the time of the photography.

For example, if the sixth fine dust concentration prediction value is closest to the correct answer value, the fine dust measurement module 117 may store a type of a converted image corresponding to the sixth fine dust concentration prediction value by matching the type with environment information, climate information, and the like at the time of photographing an image. Accordingly, it is possible to provide criteria for determining into which type of an image (i.e., converting into which image among the first converted image to the sixth converted image) to convert a photographed image based on certain environment information and climate information.

The fine dust measurement module 117 may convert images photographed in various places and time zones when training the deep learning model 117*a* to generate converted images, and train the deep learning model 117*a* by using the generated converted images as training data.

Meanwhile, here, although an example in which there is one deep learning model 117*a* has been described, but the embodiment is not limited thereto, and a deep learning model may be provided for each converted image. For example, a deep learning model corresponding to each converted image may be provided, such as a deep learning model for outputting the first fine dust concentration prediction value by using the first converted image as an input, and a deep learning model for outputting the second fine dust concentration prediction value by using the second converted image as an input.

The display module 119 may display a fine dust concentration measured by the fine dust measurement module 117 on a screen. The display module 119 may classify a value of the measured fine dust concentration into any one level among a plurality of preset levels (e.g., good, normal, bad, or the like), and display pre-stored visual representation contents on the screen according to the classified level. Here, the visual representation contents may be an image or video representing a fine dust concentration according to a level.

Figure 6:
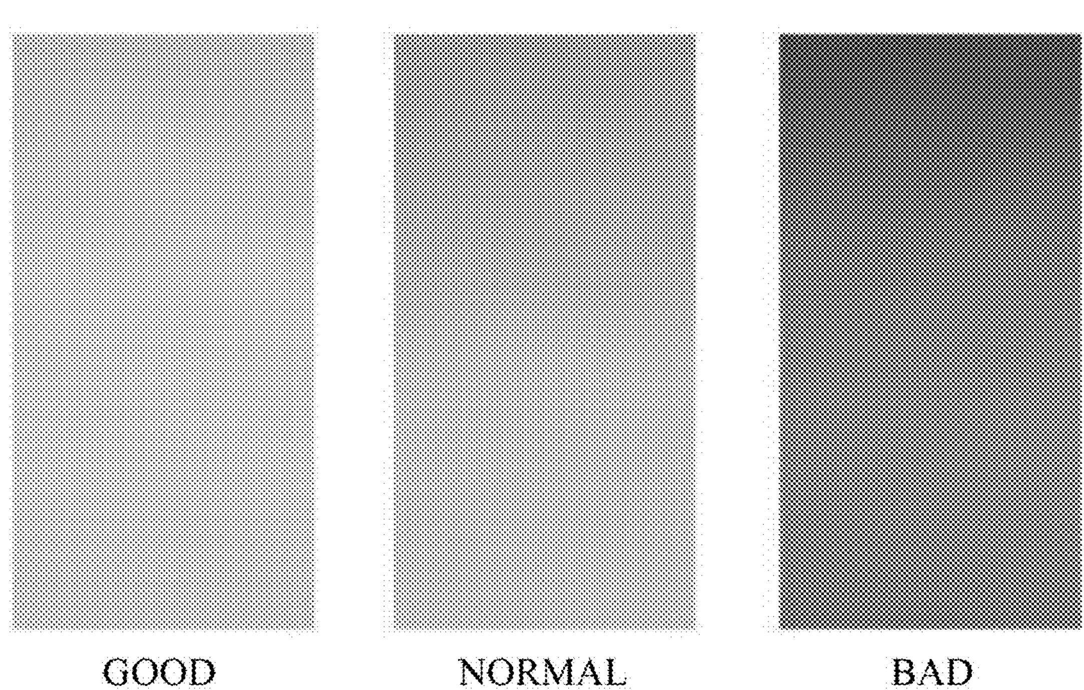
FIG. 6 is a diagram showing visual representation contents according to one embodiment of the present disclosure.

FIG. 6 is a diagram showing visual representation contents according to one embodiment of the present disclosure. Here, an example in which the visual representation content is an image is illustrated. Referring to FIG. 6, when the measured fine dust concentration value is classified into a "good" level, the display module 119 may display visual representation contents composed of a green color or a light green color on the screen. When the measured fine dust concentration value is classified into a "normal" level, the display module 119 may display visual representation contents composed of a yellow color or an orange color on the screen. When the measured fine dust concentration value is classified into a "bad" level, the display module 119 may display visual representation contents composed of a purple color of a red color on the screen.

Figure 7:
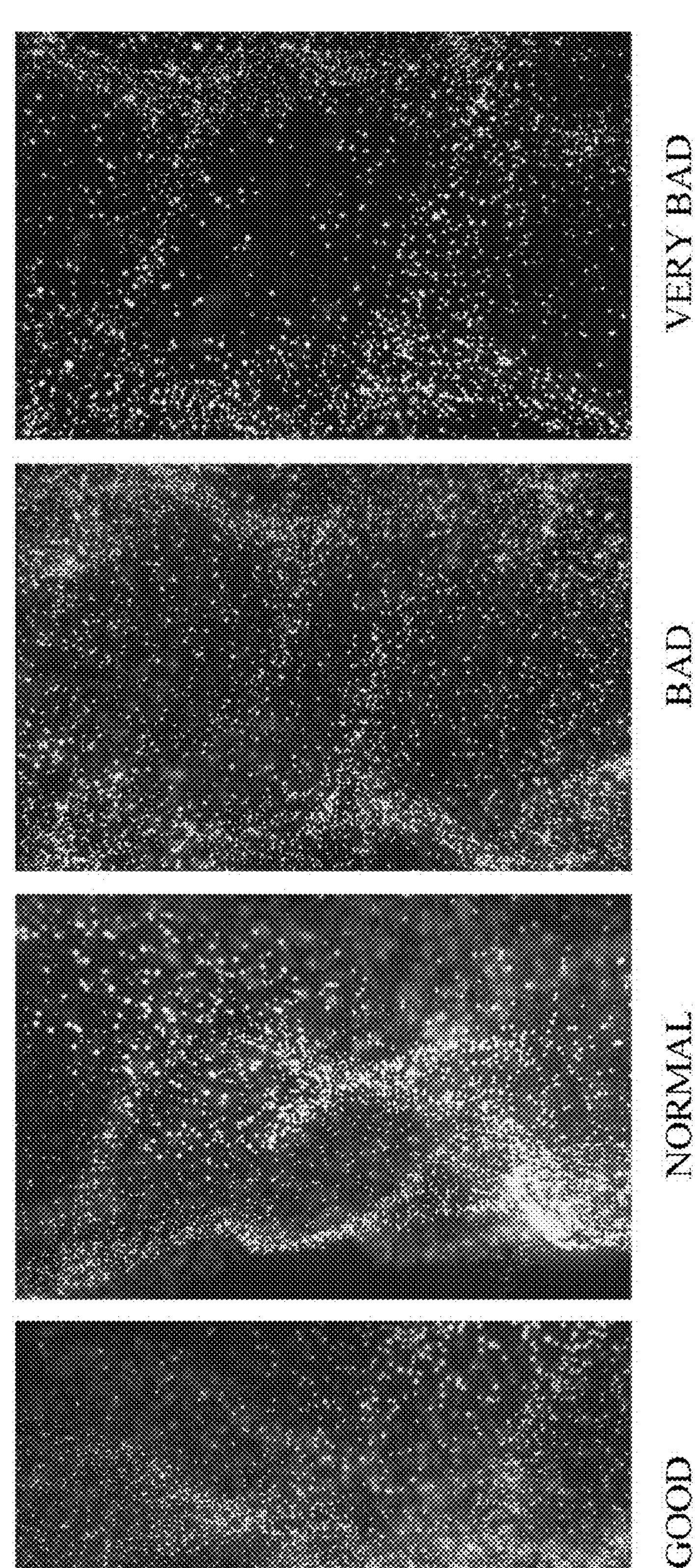
FIG. 7 is a diagram showing visual representation contents according to another embodiment of the present disclosure.

FIG. 7 is a diagram showing visual representation contents according to another embodiment of the present disclosure. In FIG. 7, a fine dust concentration is classified into four (good, normal, bad, and very bad) levels. The visual representation contents illustrated in FIG. 7 are moving images, but are represented in still images due to the limitations of being illustrated in a document. In practice, the visual representation contents may be images showing grains in each video representation content moving randomly on the screen. That is, the visual presentation contents may be displayed in the form of an interaction design which visualizes the contents in a responsive manner according to the level of a fine dust concentration or atmospheric environment index to be described later.

As described above, when a measured fine dust concentration is displayed as visual representation content, it is possible for people to easily recognize the degree of fine dust at a glance. However, the embodiment is not limited thereto, and the display module 119 may quantify a fine dust concentration value and display the same on the screen.

In addition, the display module 119 may adjust the screen brightness of the smart phone 108 based on one or more of a time zone for which a fine dust concentration is to be displayed and ambient illumination of the environment monitoring device 100. In one embodiment, the smart phone 108 may include an illumination sensor, in which case, the screen brightness of the smart phone 108 may be adjusted according to illumination measured by the illumination sensor.

The communication module 121 may serve to communicate with other devices. For example, the communication module 121 may communicate with a preset server (not shown). In addition, the communication module 121 may communicate with neighboring user terminals (not shown). In addition, the communication module 121 may communicate with other environment monitoring devices 100.

Specifically, the communication module 121 may transmit an image photographed by the photographing module 111 to a server. In one embodiment, the server may measure a fine dust concentration based on the photographed image by using deep learning technology. In addition, the communication module 121 may transmit, to the server, a fine dust concentration measured by the fine dust measurement module 117 and other environment-related information (e.g., harmful gas, air quality, fire detection, weather information, and the like) measured by using a main board to be described later.

The communication module 121 may transmit the measured fine dust concentration to a neighboring user terminal (not shown). At this time, the user terminal (not shown) may be a terminal of a user who has consented or approved to receive environment-related information from the environment monitoring device 100. In one embodiment, the communication module 121 may transmit a measured fine dust concentration to a user terminal (not shown) located within a preset distance based on a location of the environment monitoring device 100. Here, the communication module 121 has been described to transmit a fine dust concentration to a user terminal (not shown), but may further transmit other various environment-related information (e.g., harmful gas concentration, humidity, temperature, air quality information, etc.) measured by the environment monitoring device 100 to the user terminal (not shown).

In addition, the communication module 121 may be provided to communicate with other nearby environment monitoring devices 100. In one embodiment, the communication module 121 may receive a fine dust information request from other nearby environment monitoring devices 100. Specifically, when in a situation in which it is difficult for each environment monitoring device 100 to measure a fine dust concentration by itself (e.g., when a camera breaks down or a computing resource is not capable of performing a fine dust measurement process, etc.), the environment monitoring device 100 may transmit a fine dust information request to other nearby environment monitoring devices 100.

The environment monitoring device 100 may transmit one or more of a photographed image, a converted image, converted data, and a fine dust concentration measurement value to the corresponding environment monitoring device 100 in response to the fine dust information request from other environment monitoring devices 100. In one embodiment, the environment monitoring device 100 may transmit one or more of a photographed image, a converted image, converted data, and a fine dust concentration measurement value to the corresponding environment monitoring device 100 based on the degree of network communication between the environment monitoring device 100 and other environment monitoring devices 100 and hardware specification information of other environment monitoring devices 100. Each environment monitoring device 100 may store hardware specification information of other nearby environment monitoring devices 100 capable of communicating.

Here, the photographed image may mean an image photographed by a camera of the environment monitoring device 100 to measure a fine dust concentration. The converted image may be obtained by performing a first-type conversion on the photographed image. The first-type conversion may mean converting the photographed image into an image of different characteristics. For example, the first-type conversion may mean converting the photographed image into any one image among the first converted image to the sixth converted image as shown in FIG. 5.

The converted data may be obtained by performing a second-type conversion on the photographed image. The second-type conversion may mean converting the photographed image into data of different types. The second-type conversion may mean converting the photographed image to a data value.

For example, the second-type conversion may mean calculating a root mean square (RMS) contrast for the photographed image and converting the same into first converted data. The root mean square (RMS) contrast may be defined as a standard deviation of image pixel intensity. The RMS contrast may be represented by Equation 1.

$$\mathrm{RMS} = \sqrt{\frac{1}{MN}\sum_{i=1}^{N}\sum_{j=1}^{M}(I_{ij} - avg(I))^2} \quad \text{(Equation 1)}$$

$I_{ij}$: Intensity of pixel (i,j) of image in size of M×N avg(I): Average intensity of all pixels of image In addition, the second-type conversion may mean calculating entropy for the photographed image and converting the same into second converted data. Here, the entropy quantifies information included in an image and relates to an image texture, and may be calculated through Equation 2 below.

$$\mathrm{entropy} = -\sum_{i=1}^{M} p_i \log_2 p_i \quad \text{(Equation 2)}$$

$p_i$: Probability that pixel intensity is equal to i

M: Maximum intensity of image

Here, the root mean square (RMS) contrast or entropy becomes a single numerical value. As described above, the second-type conversion may include converting the photographed image into the first converted data or second converted data. The deep learning model 117*a* of each environment monitoring device 100 may be trained to measure a fine dust concentration by using the first converted data or second converted data as an input.

The environment monitoring device 100 may assign a transmission score based on the degree of network communication between the environment monitoring device 100 and other environment monitoring devices 100 and hardware specification information of other environment monitoring devices 100. Here, the transmission score may be a score for determining which data to transmit to other environment monitoring devices 100 among the captured image, the converted image, the converted data, and the fine dust concentration measurement value.

In one embodiment, the environment monitoring device 100 may assign a higher transmission score as a degree of network communication between the environment monitoring device 100 and other environment monitoring devices 100 increases, and may assign a lower transmission score as the degree of network communication degree decreases. Here, the degree of network communication may be calculated based on one or more of a network communication delay, a network bandwidth, and a network communication speed between the environment monitoring device 100 and other environment monitoring devices 100. In addition, the environment monitoring device 100 may assign a higher transmission score as performance according to hardware specification information of other environment monitoring devices 100 is better, and may assign a lower transmission score as the performance according to hardware specification information is poorer.

When the transmission score falls within a preset first range, the environment monitoring device 100 may transmit a photographed image photographed by the environment monitoring device 100 to other environment monitoring devices 100. Then, other environment monitoring devices 100 may convert the photographed image into a converted image and then input the converted image into a deep learning model to measure a find dust concentration.

When the transmission score falls within a second range, which is lower than the first range, the environment monitoring device 100 may transmit a converted image generated by performing the first-type conversion on the photographed image to other environment monitoring devices 100. Then, other environment monitoring devices 100 may input the converted image into a deep learning model to measure a find dust concentration.

When the transmission score falls within a third range, which is lower than the second range, the environment monitoring device 100 may transmit converted data generated by performing the second-type conversion on the photographed image to other environment monitoring devices 100. Then, other environment monitoring devices 100 may input the converted data into a deep learning model to measure a find dust concentration.

When the transmission score falls within a fourth range, which is lower than the third range, the environment monitoring device 100 may transmit a fine dust concentration value to other environment monitoring devices 100. Then, other environment monitoring devices 100 may display the fine dust concentration value on the screen without separate processing.

Referring back to FIG. 2 and FIG. 3, the environment monitoring device 100 may further include a main board 112. The main board 112 may be provided electrically connected to the smart phone 108. In one embodiment, the main board 112 may be provided to perform data communication with the smart phone 108 via a cable (not shown). At this time, the main board 112 may even supply power to the smart phone 108 via the cable. The main board 112 may serve to monitor other environment-related information other than the fine dust concentration.

Figure 8:
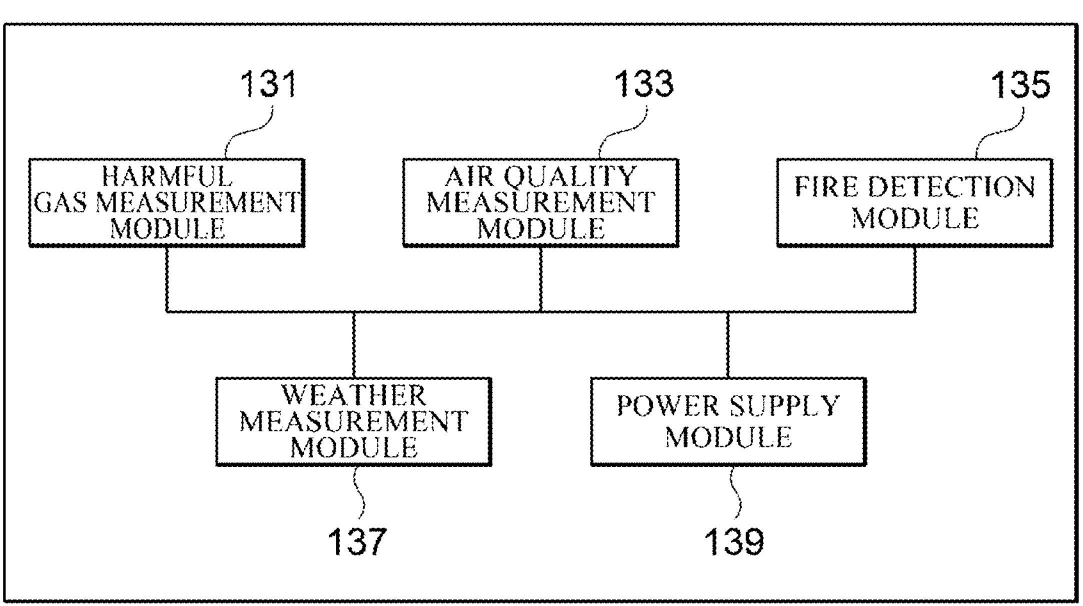
FIG. 8 is a block diagram showing a configuration of a main board according to one embodiment of the present disclosure.

FIG. 8 is a block diagram showing a configuration of the main board 112 according to one embodiment of the present disclosure. Referring to FIG. 8, the main board 112 may include a harmful gas measurement module 131, an air quality measurement module 133, a fire detection module 135, a weather measurement module 137, and a power supply module 139.

The harmful gas measurement module 131 may measure a preset harmful gas concentration around the environment monitoring device 100. In one embodiment, a harmful gas may include formaldehyde or ammonia, but is not limited thereto. The harmful gas measurement module 131 may include a sensor for measuring each harmful gas. The harmful gas measurement module 131 may transmit a harmful gas type and a measured harmful gas concentration to the smart phone 108. The smart phone 108 may display the harmful gas type and the measured harmful gas concentration on the screen.

The air quality measurement module 133 may measure air quality around the environment monitoring device 100. In one embodiment, the air quality measurement module 133 may be provided to measure the concentration of ozone, carbon monoxide, nitrogen dioxide, sulfurous acid gas, and the like. However, the embodiment is not limited thereto, and the air quality measurement module 133 may be provided to measure the concentration of fine dust (PM 10) and ultra-fine dust (PM 2.5).

The air quality measurement module 133 may include a sensor for measuring the concentration of ozone, carbon monoxide, nitrogen dioxide, sulfurous acid gas, and the like. The air quality measurement module 133 may measure a concentration of a corresponding pollutant for a preset time (e.g., 1 hour or 24 hours, etc.). The air quality measurement module 133 may calculate an atmospheric environment index based on the concentration of the pollutant (e.g., ozone, carbon monoxide, nitrogen dioxide, sulfurous acid gas, etc.) measured for the preset time, and classify a level of the corresponding pollutant into any one level among a plurality of preset levels according to a calculated atmospheric environment index value. The atmospheric environment index may be calculated by Equation 3.

$$I_p = \frac{I_{HI} - I_{LO}}{BP_{HI} - BP_{LO}} \times (C_p - BP_{LO}) + I_{LO} \quad \text{(Equation 3)}$$

$I_p$: Atmospheric environment index of target pollutant $C_p$: Concentration of target pollutant in the atmosphere $BP_{HI}$: Maximum pollution level set at each level of target pollutant $BP_{LO}$: Minimum pollution level set at each level of target pollutant $I_{HI}$: Atmospheric environment index value corresponding to $BP_{HI}$ $I_{LO}$: Atmospheric environment index value corresponding to $BP_{LO}$ In Equation 3, $BP_{HI}$ and $BP_{LO}$ may be differently set according to the type of a target pollutant. In one embodiment, the level of a pollutant may be classified as "good" if the atmospheric environment index is 0 to 50, may be classified as "normal" if the atmospheric environment index is 51 to 100, may be classified as "bad" if the atmospheric environment index is 101 to 250, and may be classified as "very bad" if the atmospheric environment index is 251 to 500. For example, if the level of a pollutant is "good," $I_{LO}$ becomes 0 and $I_{HI}$ becomes 50.

The air quality measurement module 133 may transmit the measured type and level of a pollutant to the smart phone 108. Then, the smart phone 108 may display visual representation contents on the screen as shown in FIG. 7 according to the measured level of the pollutant.

The fire detection module 135 may detect a fire around the environment monitoring device 100. The fire detection module 135 may include a sensor for detecting heat or smoke, a sensor for detecting a burning smell from a fire, and the like. In one embodiment, the fire detection module 135 may sense a fire in conjunction with a camera of the smart phone 108. At this time, the fire detection module 135 may detect a fire based on data measured by a sensor and an image photographed by the camera.

The fire detection module 135 may generate a fire alarm when detecting a fire. In addition, the fire detection module 135 may transmit the detection of a fire to the smart phone 108 when detecting the fire. Then, smart phone 108 may generate a fire alarm. The generation of the fire alarm may be performed by one or more means of a warning sound and a warning light. The smart phone 108 may also transmit the detection of a fire to a nearby user terminal (not shown).

The weather measurement module 137 may measure preset weather factors around the environment monitoring device 100. Here, the weather factors may include temperature, humidity, wind speed, wind volume, precipitation, atmospheric pressure, and the like. The weather measurement module 137 may include a sensor for measuring the weather factors. The weather measurement module 137 may transmit a weather factor type and a measured weather factor value to the smart phone 108. The smart phone 108 may display the weather factor type and the measured weather factor value on the screen.

The power supply module 139 may supply power to the environment monitoring device 100. In one embodiment, the power supply module 139 may include a solar panel and a battery. The power supply module 139 may charge the battery with electrical energy generated from the solar panel. The power supply module 139 may supply power to the environment monitoring device 100 through the energy charged in the battery. The power supply module 139 may monitor a remaining battery amount of the smart phone 108, and supply power to the smart phone 108 when the remaining battery amount becomes less than a preset threshold value, thereby charging the battery of the smart phone 108.

According to embodiments of the present disclosure, fine dust is measured using a smart phone 108 to be discarded, so that it is possible to reuse the smart phone 108, thereby effectively solving an electronic waste problem. In addition, by measuring fine dust based on an image, it is possible to easily measure fine dust at a low cost and may display fine dust information surrounding people.

In the present specification, the term "module" may mean a functional and structural coupling of hardware for performing the technical idea of the present disclosure and software for driving the hardware. For example, the "module" may mean a logical unit of a predetermined code and a hardware resource for executing the predetermined code, and does not necessarily mean a physically connected code, or one type of hardware.

Figure 9:
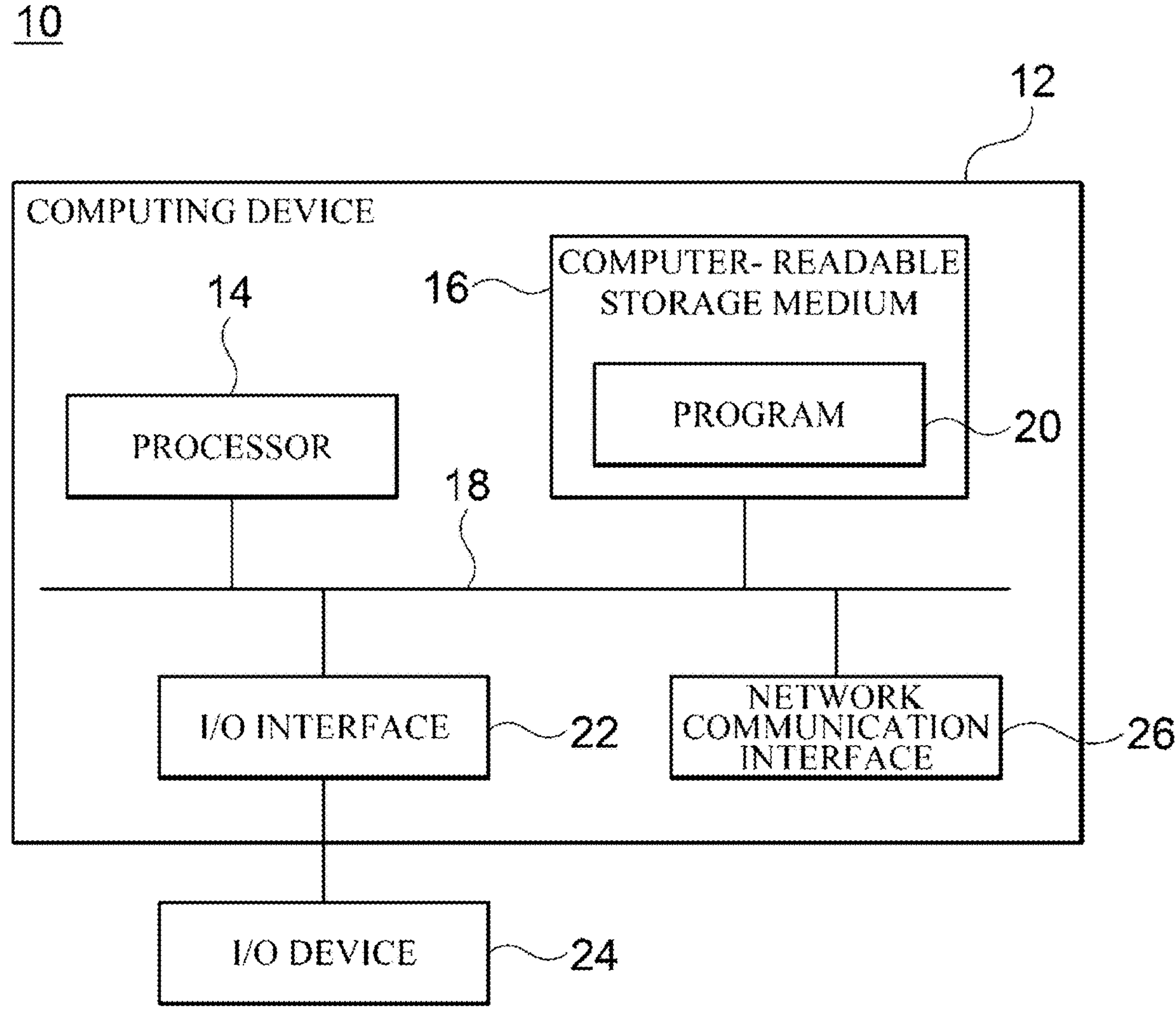
FIG. 9 is a block diagram for illustrating and describing a computing environment including a computing device suitable to be used in exemplary embodiments.

FIG. 9 is a block diagram for describing an example of a computing environment 10 including a computing device suitable for being used in example embodiments. In the illustrated embodiment, each component may have different functions and capabilities in addition to those described below, and additional components may be included in addition to those described below.

The illustrated computing environment 10 includes a computing device 12. In an embodiment, the computing device 12 may be the environment monitoring device 100. In addition, the computing device 12 may be the smart phone 108.

The computing device 12 includes at least one processor 14, a computer-readable storage medium 16, and a communication bus 18. The processor 14 may enable the computing device 12 to operate according to the exemplary embodiment mentioned above. For example, the processor 14 may execute one or more programs stored in the computer-readable storage medium 16. The one or more programs may include one or more computer-executable commands, and when executed by the processor 14, the computer-executable command may be configured to enable the computing device 12 to perform operations according to the exemplary embodiment.

The computer-readable storage medium 16 is configured to store computer-executable commands or program codes, program data, and/or other suitable types of information. A program 20 stored in the computer-readable storage medium 16 includes a set of commands executable by the processor 14. In an embodiment, the computer-readable storage medium 16 may be a memory (a volatile memory such as a random access memory, a non-volatile memory, or a suitable combination thereof), one or more magnetic disk storage devices, optical disk storage devices, flash memory devices, other types of storage media accessed by the computing device 12 and capable of storing desired information, or any suitable combination thereof.

The communication bus 18 includes the processor 14 and the computer-readable storage medium 16 to interconnect various other components of the computing device 12.

The computing device 12 may also include one or more input/output interfaces 22 which provide an interface for one or more input/output devices 24, and one or more network communication interfaces 26. The input/output interface 22 and the network communication interface 26 are connected to the communication bus 18. The input/output device 24 may be connected to other components of the computing device 12 through the input/output interface 22. The exemplary input/output device 24 may include a pointing device (such as a mouse or track pad), a keyboard, a touch input device (such as a touch pad or touch screen), a voice or sound input device, an input device such as various types of sensor devices and/or photographing devices, and/or an output device such as a display device, a printer, a speaker, and/or a network card. The exemplary input/output device 24 may be included inside the computing device 12 as one component constituting the computing device 12, or may be connected to the computing device 12 as a separate device distinct from the computing device 12.

According to embodiments of the present disclosure, fine dust is measured using a smart phone to be discarded, so that it is possible to reuse the smart phone, thereby effectively solving an electronic waste problem. In addition, by measuring fine dust based on an image, it is possible to easily measure fine dust at a low cost and may display fine dust information surrounding people.

Although the exemplary embodiments of the present invention has been described in detail as above, those skilled in the art to which the present invention pertains will understand that various modifications may be made thereto within the limit that do not depart from the scope of the present invention. Therefore, the scope of rights of the present invention should not be limited to the described embodiments, but should be defined not only by claims set forth below but also by equivalents of the claims.

What is claimed is:

1. An environment monitoring device to be installed indoors or outdoors, the environment monitoring device comprising:

a first case;

a second case coupled to the first case; and a smart phone provided fixed in an inner space between the first case and the second case, wherein the smart phone is configured to measure a fine dust concentration around the environment monitoring device based on an image photographed with a camera, and display information on the measured fine dust concentration via a screen of the smart phone, wherein the first case comprises a first opening provided corresponding to the size of a screen of the smart phone to expose the screen of the smart phone to the outside; and the second case is coupled to the first case at the rear of the first case, and comprises a second opening provided corresponding to the camera of the smart phone, wherein the environment monitoring device comprises a smart phone support configured to fixedly support the smart phone between the first case and the second case, wherein the smart phone support includes:

a first support provided with a third opening to allow the smart phone to be inserted thereinto and received therein; and a second support configured to support the smart phone in front of the first support, and provided with a fourth opening corresponding to the size of the screen of the smart phone.

2. The environment monitoring device of claim 1, wherein the environment monitoring device further comprises:

a heat dissipation part provided on the back surface of the second case and provided to emit heat generated from the smart phone to the outside; and a gap formed in a frame of the first support.

3. The environment monitoring device of claim 1, wherein the smart phone comprises:

a photographing module including the camera, and allowing the camera to photograph the front;

a conversion module configured to convert all or a part of a photographed image of the photographing module into an image having different characteristics so as to generate one or more converted images;

a fine dust measurement module configured to input the converted image to a pre-trained deep learning model so as to measure a fine dust concentration at a target point of photography; and a display module configured to display information on the measured fine dust concentration on a screen.

4. The environment monitoring device of claim 3, wherein the display module is configured to classify a value of the measured fine dust concentration into any one level among a plurality of preset levels, and display pre-stored visual representation contents on the screen according to the classified level.

5. The environment monitoring device of claim 3, wherein the fine dust measurement module is configured to:

input a plurality of converted images of different types to the deep learning model when training the deep learning model to respectively output fine dust concentration prediction values for the plurality of converted images, and train the deep learning model to minimize the difference between each fine dust concentration prediction value and a correct answer value; and extract a prediction value closest to the correct answer value among the fine dust concentration prediction values, and store a type of a converted image corresponding to the extracted prediction value by matching the type with one or more of information selected from the group consisting of environment information and climate information at the time of the photography.

6. The environment monitoring device of claim 5, wherein the conversion module is configured to acquire the one or more of the information selected from the group consisting of the environment information and climate information at the time of the photography, determine into what type of an image to convert all or a part of the photographed image based on one or more of the acquired environment information and climate information, and generate a converted image by converting all or a part of the photographed image into an image of the determined type.

7. The environment monitoring device of claim 1, wherein the smart phone comprises:

a photographing module including the camera, and allowing the camera to photograph the front;

a conversion module configured to perform a first-type conversion for converting all or a part of a photographed image of the photographing module into an image of different characteristics to generate a converted image, or perform a second-type conversion for converting all or a part of a photographed image into data of different types to generate converted data; and a fine dust measurement module configured to input the converted image or the converted data to a pre-trained deep learning model to measure a fine dust concentration at a target point of photography.

8. The environment monitoring device of claim 7, wherein the environment monitoring device is provided to be able to communicate with one or more other environment monitoring devices installed in the vicinity of the environment monitoring device, and provided to receive a fine dust information request from other environment monitoring devices.

9. The environment monitoring device of claim 8, wherein the environment monitoring device is configured to transmit one or more of an element selected from the group consisting of a photographed image, a converted image, converted data, and a fine dust concentration measurement value to other environment monitoring devices in response to the fine dust information request from other environmental monitoring devices.

10. The environment monitoring device of claim 9, wherein the environment monitoring device is configured to transmit the one or more of the element selected from the group consisting of the photographed image, the converted image, the converted data, and the fine dust concentration measurement value to other environment monitoring devices based on a degree of network communication between the environment monitoring device and other environment monitoring devices and hardware specification information of other environment monitoring devices.

11. The environment monitoring device of claim 10, wherein the environment monitoring device is configured to assign a transmission score based on the degree of network communication and the hardware specification information of other environment monitoring devices, and transmit the photographed image when the transmission score falls within a preset first range, transmit the converted image when the transmission score falls within a second range lower than the first range, transmit the converted data when the transmission score falls within a third range lower than the second range, and transmit the fine dust concentration measurement value when the transmission score falls within a fourth range lower than the third range.

12. The environment monitoring device of claim 1, wherein the environment monitoring device is provided to perform data communication with the smart phone, is provided to monitor other environment-related information other than the fine dust concentration, and further comprises a main board configured to display other environment-related information using the smart phone.

13. The environment monitoring device of claim 12, wherein the main board comprises:

a harmful gas measurement module configured to measure a preset harmful gas concentration around the environment monitoring device;

an air quality measurement module configured to measure air quality around the environment monitoring device;

a fire detection module configured to detect a fire around the environment monitoring device;

a weather measurement module configured to measure a preset weather factor around the environment monitoring device; and a power supply module configured to supply power to the environment monitoring device.

* * * * *